(12) United States Patent
Sakuma et al.

(10) Patent No.: US 9,176,093 B2
(45) Date of Patent: Nov. 3, 2015

(54) GAS SENSOR

(71) Applicant: NGK SPARK PLUG CO., LTD., Nagoya-shi, Aichi (JP)

(72) Inventors: Shun Sakuma, Inuyama (JP); Masaki Mizutani, Aichi (JP); Makoto Shimoide, Aichi (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 133 days.

(21) Appl. No.: 13/782,336

(22) Filed: Mar. 1, 2013

(65) Prior Publication Data

US 2013/0233708 A1    Sep. 12, 2013

(30) Foreign Application Priority Data

Mar. 6, 2012   (JP) ................................. 2012-049294

(51) Int. Cl.
*G01N 27/407*   (2006.01)

(52) U.S. Cl.
CPC ................................. *G01N 27/4071* (2013.01)

(58) Field of Classification Search
CPC ..... G01M 15/10; G01M 15/02; G01M 15/04; G01N 1/2252; G01N 27/406–27/407; G01N 27/409; G01N 27/419; G01N 27/41; F02D 41/1483; F02D 41/1461; F02D 41/1474; F02D 41/146; F01N 2560/00
USPC ................................................ 204/421–429
See application file for complete search history.

(56) References Cited

U.S. PATENT DOCUMENTS

| | | |
|---|---|---|
| 5,144,249 A | 9/1992 | Kurishita et al. |
| 6,645,360 B1 | 11/2003 | Eisele et al. |
| 7,494,400 B2 | 2/2009 | Kawashima |
| 2004/0158971 A1 | 8/2004 | Kawashima |
| 2008/0067067 A1* | 3/2008 | Oya et al. ..................... 204/426 |
| 2008/0202205 A1 | 8/2008 | Suzuki et al. |
| 2008/0302661 A1* | 12/2008 | Suzuki et al. ................ 204/424 |

FOREIGN PATENT DOCUMENTS

| | | |
|---|---|---|
| DE | 19815174 | * 10/1999 |
| JP | 3-272448 A | 12/1991 |
| JP | 2000-025025 A | 1/2000 |
| JP | 2003-502664 A | 1/2003 |
| JP | 2004-251654 A | 9/2004 |
| JP | 2006-201191 A | 8/2006 |
| JP | 2008-139270 A | 6/2008 |
| JP | 2008-209300 A | 9/2008 |
| JP | 2009-002810 A | 1/2009 |
| JP | 2011-257433 A | 12/2011 |

OTHER PUBLICATIONS

Machine Translation JP 2000-025025, done Sep. 5, 2014.*
Machine Translation DE 19815174, done Feb. 25, 2015.*
Japanese Office Action dated Mar. 11, 2014 in the corresponding Japanese Patent Application No. 2012-049294.

* cited by examiner

*Primary Examiner* — Jennifer Dieterle
(74) *Attorney, Agent, or Firm* — Sughrue Mion, PLLC

(57) ABSTRACT

A gas sensor element having a chamfered portion. The chamfered portion has a leading end chamfered portion formed in a leading end portion of the gas sensor element, a rear end chamfered portion formed in a rear end portion of the gas sensor element, and an intermediate chamfered portion linking the leading end chamfered portion and rear end chamfered portion. The chamfer angle of the rear end chamfered portion is formed so as to be larger than the chamfer angle of the leading end chamfered portion.

10 Claims, 9 Drawing Sheets

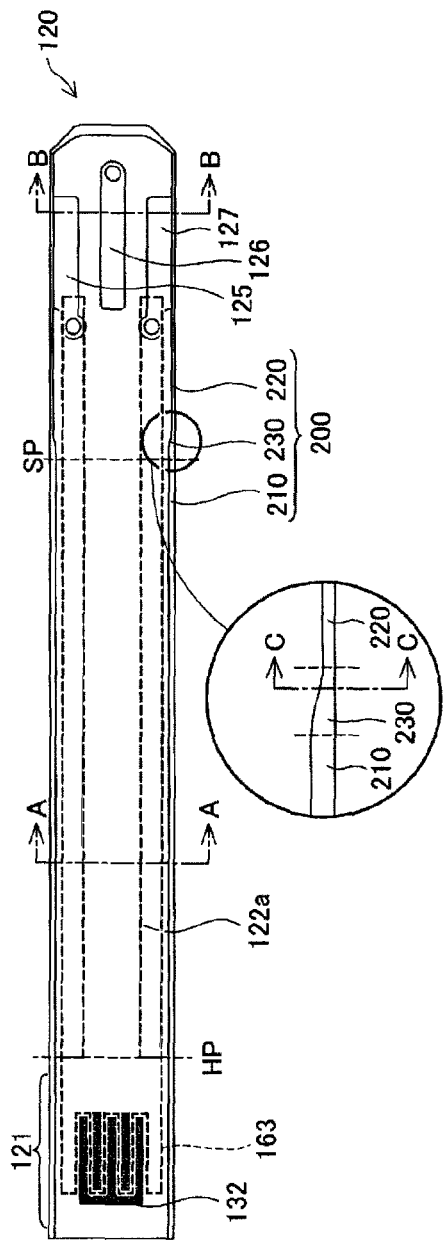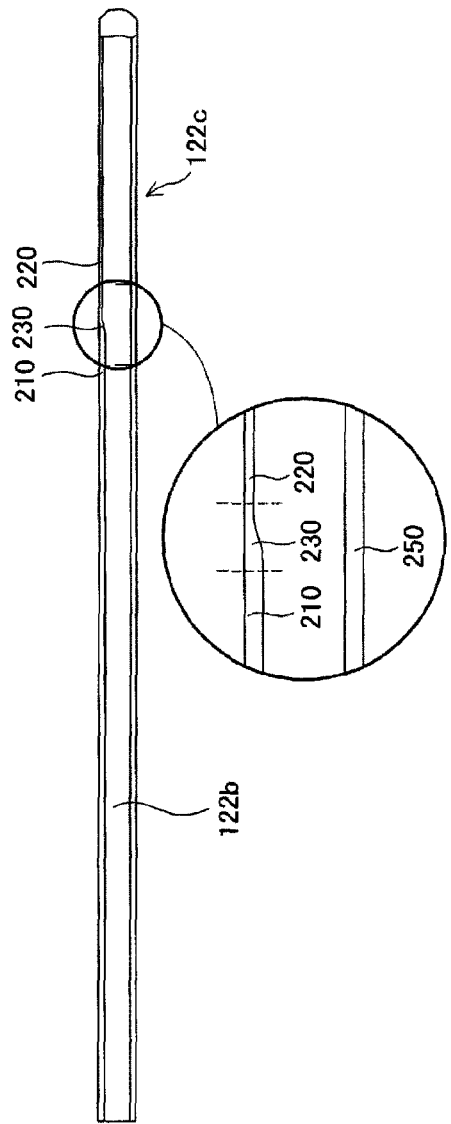

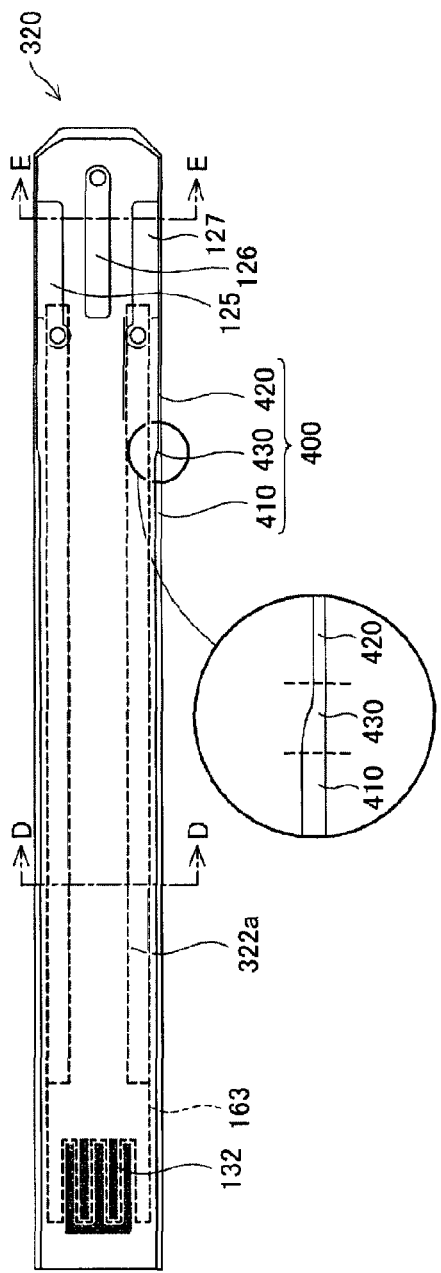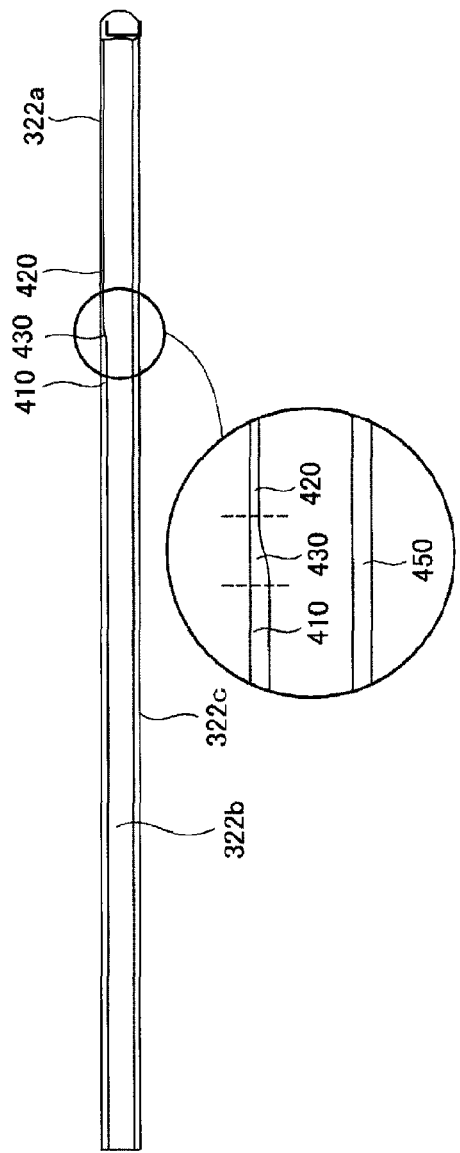

GAS SENSOR

BACKGROUND OF THE INVENTION

1. Field of the Invention

The present invention relates to a gas sensor including a plate-like gas sensor element.

2. Description of the Related Art

As a gas sensor that carries out detection and measurement of the concentration of a specified gas component contained in an exhaust gas of an internal-combustion engine or the like, one including a plate-type gas sensor wherein a plurality of substrates are stacked one on another has heretofore been known. The gas sensor element has a sensing portion provided in a leading end portion thereof, and carries out a detection and measurement of the concentration of a specified gas component by exposing the sensing portion to an exhaust gas. Also, in this kind of gas sensor, electrode pads for outputting a detection signal from the sensing portion to an external circuit are disposed on a surface in a rear end portion of the gas sensor element. Furthermore, a technology is known wherein a ridge line (between a surface of the gas sensor element on which the electrode pads are provided and a side surface perpendicular to the surface) is chamfered and ground, thereby eliminating a surface defect, such as a burr formed at the ridge line when manufacturing the element. This measure can suppress damage such as a crack or chipping caused by a shock from outside the gas sensor element. For example, in JP-A-2004-251654, a chamfered portion is provided by chamfering a ridge line, provided in a longitudinal direction of a gas sensor element, uniformly at a chamfer angle of 45°.

A chamfer angle and chamfer amount are specified for the chamfered portion from the standpoint of imparting thermal shock resistance to a leading end portion of the gas sensor element exposed to an exhaust gas. Further, a chamfered portion uniform in the longitudinal direction of the gas sensor element, also including a rear end portion of the gas sensor element, is provided.

However, when this kind of chamfered portion is provided in a gas sensor element on a surface of which a plurality of electrode pads are disposed, the area of the surface (the width of the surface) in the rear end portion on which the electrode pads are disposed is reduced. This makes it necessary to further shorten the distances between the electrode pads. Because of this, there is a danger of bringing about a decrease in the insulating performance between the electrode pads. On the other hand, when the distances between the electrode pads are secured by reducing the area of the electrode pads in order to secure the insulating performance between the electrode pads, there is a danger that the contactability between the electrode pads and connection terminals decreases.

SUMMARY OF THE INVENTION

The present invention has been made to solve the heretofore described problems, and an object thereof is to maintain the thermal shock resistance of a leading end portion of a gas sensor element while suppressing damage to a ridge line of the gas sensor element, as well as to improve the insulating properties between electrode pads disposed in a rear end portion of the gas sensor element, and to secure the contactability between the electrode pads and connection terminals.

The above object has been achieved, in a first aspect (1) of the invention, by providing a gas sensor comprising a gas sensor element including a plate-shaped detecting element extending in a longitudinal direction, a sensing portion disposed in a leading end portion in the longitudinal direction of the detecting element and detecting a specified gas in a gas to be measured, and a plurality of electrode pads disposed on an outer surface in a rear end portion in the longitudinal direction of the detecting element, at least one of the electrode pads outputting a detection signal from the sensing portion to an external circuit; and a housing that encloses the periphery of the gas sensor element. The gas sensor element has at least one chamfered portion linking a first outer surface and a second surface of the detecting element, the first outer surface extending in the longitudinal direction and having the electrode pads disposed thereon, and the second outer surface extending in the longitudinal intersecting the first outer surface. The chamfer angle of the chamfered portion to the first outer surface is formed so that the chamfer angle of a rear end chamfered portion provided in the rear end portion is larger than the chamfer angle of a leading end chamfered portion provided in the leading end portion. The electrode pads are arranged adjacent to the chamfered portions.

According to the gas sensor (1) above, the gas sensor element is such that the chamfered portion chamfered all along the longitudinal direction is formed between the first outer surface and second outer surface. Consequently, it is possible to suppress damage, such as a chipping or cracking, to the gas sensor element. Also, the chamfered portion of the gas sensor element is such that the chamfer angle of the rear end chamfered portion formed in the rear end portion in which the electrode pad is disposed is larger than the chamfer angle of the leading end chamfered portion formed in the leading end portion in which the sensing portion is provided. Consequently, it is possible to increase the area of the first outer surface (the width of the first outer surface) in the rear end portion of the gas sensor element as compared with the area of the first outer surface (the width of the first outer surface) in the leading end portion, and it is not necessary to shorten the distances between the electrode pads. Therefore, it is possible to secure the insulating properties between the plurality of electrode pads. Also, it is not necessary to secure the distances between the electrode pads by reducing the area of the electrode pads, and it is possible to secure the contactability between the electrode pads and connection terminals. Furthermore, as the chamfer angle of the leading end chamfered portion is made smaller than the chamfer angle of the rear end chamfered portion, it is possible to adequately secure the size of the leading end chamfered portion, and it is possible to adequately maintain the thermal shock resistance of the leading end portion of the gas sensor element exposed to an exhaust gas.

Also, the electrode pads are provided so as to be adjacent to the chamfered portions. As used herein, "adjacent" means that no space or other member exists between the chamfered portions and respective electrode pads. By so doing, it is possible to secure the contactability between the electrode pads and connection terminals, with high accuracy, even when a displacement occurs in the positions of the connection terminals relative to the gas sensor element. Also, it is possible to increase the area of the electrode pads to the maximum possible without shortening the distances between the electrode pads. Therefore, it is possible to secure the contactability between the electrode pads and connection terminals while securing the insulating properties between the plurality of electrode pads.

In a preferred embodiment (2) of the gas sensor according to (1) above, the chamfer angle of the chamfered portion is 30° or more.

According to the gas sensor (2), the chamfered portion is chamfered at a chamfer angle of 30° or more. Consequently, it is possible to adequately maintain the thermal shock resistance of the sensor element.

In another preferred embodiment (3) of the gas sensor according to (1) or (2) above, the chamfered portion has an intermediate chamfered portion that is formed between the rear end chamfered portion and leading end chamfered portion, and the intermediate chamfered portion is chamfered at a chamfer angle equal to or smaller than the chamfer angle of the rear end chamfered portion and equal to or larger than the chamfer angle of the leading end chamfered portion.

According to the gas sensor (3), the intermediate chamfered portion chamfered at a chamfer angle equal to or smaller than the chamfer angle of the rear end chamfered portion and equal to or larger than the chamfer angle of the leading end chamfered portion is formed between the rear end chamfered portion and leading end chamfered portion. Consequently, it is possible to reduce the difference in chamfer angle between the rear end chamfered portion and leading end chamfered portion without producing a step in the boundary portion between the rear end chamfered portion and leading end chamfered portion, and it is possible to suppress damage to the boundary portion due to a shock from the exterior.

In yet another preferred embodiment (4), the gas sensor according to (3) above further comprises: a separator, disposed so as to cover the rear end portion of the gas sensor element, and in which output terminals connected to the electrode pads are provided. The intermediate chamfered portion is formed so as to be positioned closer to a rear end side in the longitudinal direction than a leading end position of the separator.

According to the gas sensor (4), the intermediate chamfered portion is formed so as to be positioned closer to the rear end side in the longitudinal direction than the leading end position of the separator. Consequently, because the leading end chamfered portion with a chamfer angle large compared with those of the intermediate chamfered portion and rear end chamfered portion is formed in an exposed portion of the sensor element not covered with the separator, it is possible to suppress damage to the exposed portion of the sensor element.

In yet another preferred embodiment (5), the gas sensor according to (3) or (4) above further comprises a heater element, disposed in the longitudinal direction of the gas sensor element, and having at least a heating resistor disposed in the leading end portion thereof, stacked on the detecting element, wherein the intermediate chamfered portion is formed so as to be positioned closer to the rear end side in the longitudinal direction than a rear end position of the heating resistor.

According to the gas sensor (5), the intermediate chamfered portion is formed so as to be positioned closer to the rear end side in the longitudinal direction than the rear end position of the heat resistor. Consequently, because the leading end chamfered portion with a chamfer angle large compared with those of the intermediate chamfered portion and rear end chamfered portion is formed in the leading end portion in which the heat resistor is provided, it is possible to adequately maintain the thermal shock resistance of the leading end portion of the sensor element even when the leading end portion is affected by heat from the heat resistor.

In yet another preferred embodiment (6) of the gas sensor according to any one of (3) to (5) above, the intermediate chamfered portion is formed so that the chamfer angle increases from a leading end side toward the rear end side in the longitudinal direction.

According to the gas sensor (6), the intermediate chamfered portion is formed so that the chamfer angle increases from the leading end side toward the rear end side in the longitudinal direction. Consequently, by smoothly linking the rear end chamfered portion and leading end chamfered portion, it is possible to prevent a ridge portion from being formed between the rear end chamfered portion and leading end chamfered portion, and it is possible to suppress damage to the boundary portion between the rear end chamfered portion and leading end chamfered portion.

In yet another preferred embodiment (7) of the gas sensor according to any one of (1) to (6) above, the chamfer length of the leading end chamfered portion is 0.1 mm or more.

According to the gas sensor (7), the chamfer length of the leading end chamfered portion is 0.1 mm or more. Consequently, it is possible to adequately secure the thermal shock resistance of the sensor element.

In a second aspect (8), the invention provides a gas sensor comprising a gas sensor element including a plate-shaped detecting element extending in a longitudinal direction, a sensing portion disposed in a leading end portion in the longitudinal direction of the detecting element and detecting a specified gas in a gas to be measured, and a plurality of electrode pads disposed on an outer surface in a rear end portion in the longitudinal direction of the detecting element, at least one of the electrode pads outputting a detection signal from the sensing portion to an external circuit; and a housing that encloses the periphery of the gas sensor element. The gas sensor element has at least one chamfered portion linking a first outer surface and a second outer surface of the detecting element, the first outer surface extending in the longitudinal direction and having the electrode pads disposed thereon, and the second outer surface extending in the longitudinal and intersecting the first outer surface. A chamfer length of the chamfered portion in a direction parallel to the first outer surface is formed so that the chamfer length of a rear end chamfered portion provided in the rear end portion is shorter than the chamfer length of a leading end chamfered portion provided in the leading end portion. The electrode pads are arranged adjacent to the chamfered portions.

According to the gas sensor (8), the gas sensor element is such that the chamfered portion chamfered all along the longitudinal direction is formed between the first outer surface and second outer surface. Consequently, it is possible to suppress damage, such as a chipping or cracking, to the gas sensor element. Also, the chamfered portion of the gas sensor element is such that the chamfer length of the rear end chamfered portion formed in the rear end portion in which the electrode pads are disposed is shorter than the chamfer length of the leading end chamfered portion formed in the leading end portion in which the sensing portion is provided. Consequently, it is possible to increase the area of the first outer surface (the width of the first outer surface) in the rear end portion of the gas sensor element as compared with the area of the first outer surface (the width of the first outer surface) in the leading end. Further, it is not necessary to shorten the distances between the electrode pads, and it is possible to secure the insulating properties between the plurality of electrode pads. Also, it is not necessary to secure the distances between the electrode pads by reducing the area of the electrode pads, and it is possible to secure the contactability between the electrode pads and connection terminals. Furthermore, as the chamfer length of the leading end chamfered portion is made larger than the chamfer length of the rear end chamfered portion, it is possible to adequately secure the size of the leading end chamfered portion, and it is possible to adequately maintain the thermal shock resistance of the leading end portion of the gas sensor element exposed to an exhaust gas.

Also, the electrode pads are arranged adjacent to the chamfered portions. By so doing, it is possible to secure the contactability between the electrode pads and connection terminals, with high accuracy, even when a displacement occurs in the positions of the connection terminals relative to the sensor element. Also, it is possible to increase the area of the electrode pads to the maximum possible without shortening the distances between the electrode pads, and it is possible to secure the contactability between the electrode pads and connection terminals while securing the insulating properties between the plurality of electrode pads.

In a preferred embodiment (9) of the gas sensor according to (8) above, the chamfer length of the leading end chamfered portion is 0.1 mm or more.

According to the gas sensor (9), the chamfer length of the leading end chamfered portion is 0.1 mm or more. Consequently, it is possible to adequately secure the thermal shock resistance of the sensor element.

In another preferred embodiment (10) of the gas sensor according to (8) or (9) above, the chamfer angle of the chamfered portion is 30° or more.

According to the gas sensor (10), the chamfered portion is chamfered at a chamfer angle of 30° or more. Consequently, it is possible to adequately secure the thermal shock resistance of the sensor element.

In the invention, the heretofore described various aspects can be applied by being combined or partially omitted when appropriate.

BRIEF DESCRIPTION OF THE DRAWINGS

FIGS. 5A and 5B illustrate a chamfered portion 200 of the first embodiment.

FIGS. 10A and 10B illustrate a gas sensor element 320 in a second embodiment.

DETAILED DESCRIPTION OF THE EMBODIMENTS

The invention is now described in detail by reference to the drawings. However, the present invention should not be construed as being limited thereto.

A. FIRST EMBODIMENT

A1. Configuration of Gas Sensor

Figure 1:
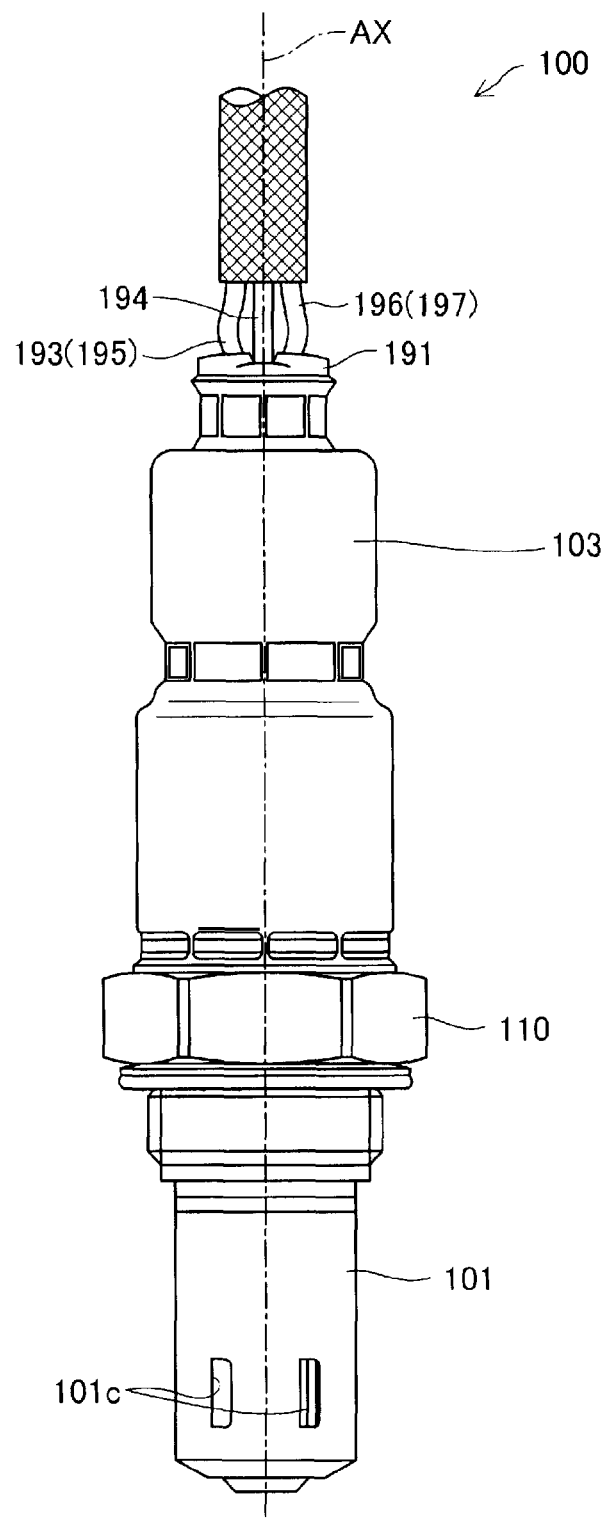
FIG. 1 is an external view of a gas sensor 100 in a first embodiment.
Figure 2:
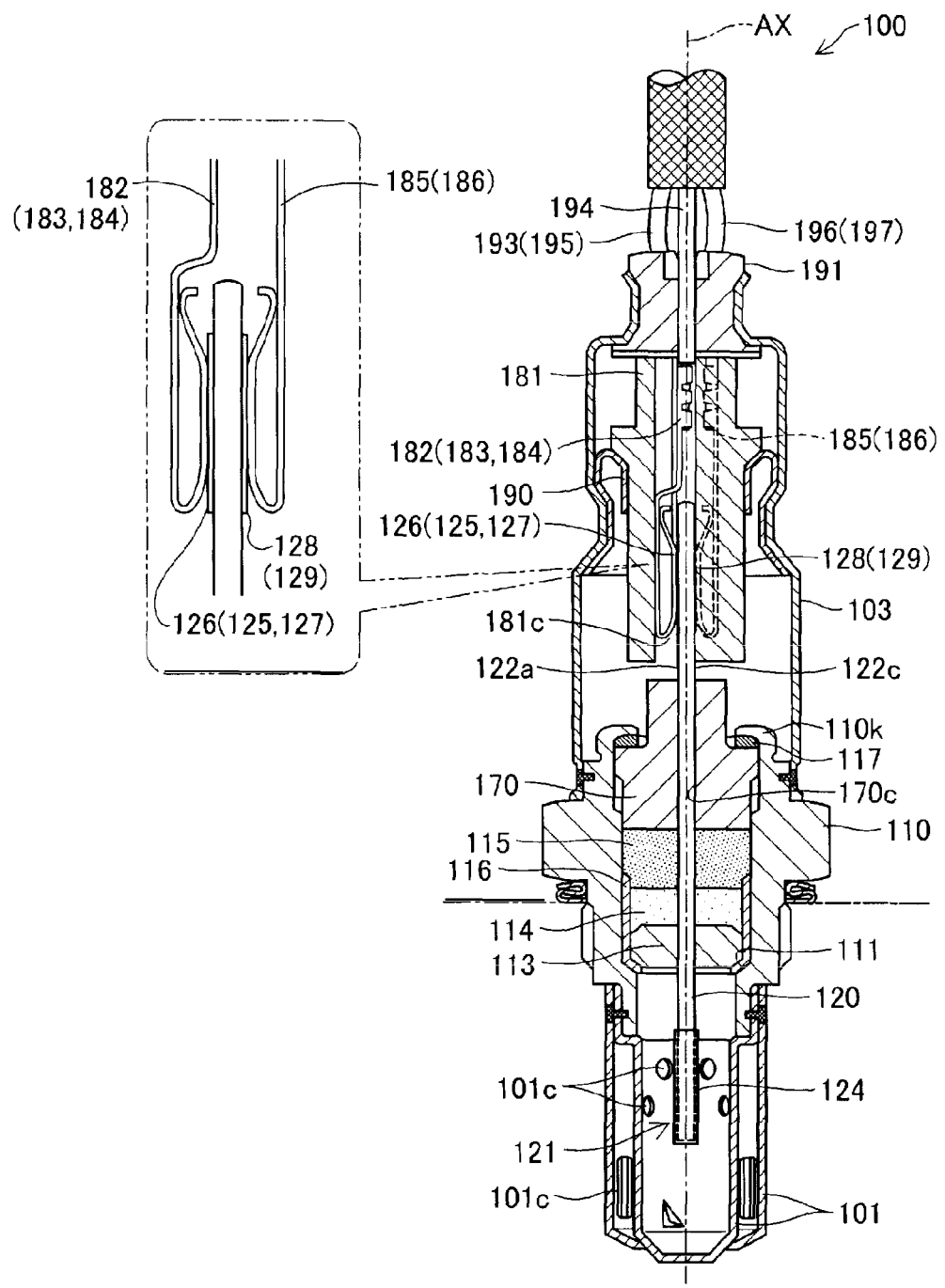
FIG. 2 is a sectional view of the gas sensor 100 of the first embodiment.

FIG. 1 is an external view of a gas sensor 100 according to one embodiment of the invention. FIG. 2 is a sectional view of the gas sensor 100. In FIGS. 1 and 2, the lower side in the drawings refers to a leading end side in a direction of an axis AX, and the upper side in the drawings refers to a rear end side in the axis AX direction. The gas sensor 100, by being mounted in an exhaust pipe of an internal-combustion engine, is used as a full-range air-fuel sensor that linearly detects the concentration of oxygen in an exhaust gas. An electronic control unit (not shown) mounted on a vehicle, based on the concentration of oxygen detected by the gas sensor 100, carries out feedback control of the air-fuel ratio of a mixture supplied to the internal-combustion engine.

As shown in FIGS. 1 and 2, the gas sensor 100 includes a cylindrical metal shell 110 (that corresponds to a "housing" of the invention) extending in the axis AX direction, a gas sensor element 120 disposed on the inner side of the metal shell 110, a cylindrical ceramic sleeve 170 that supports the gas sensor element 120 by having inserted therein the gas sensor element 120, and a separator 181 fitted on the rear end side of the gas sensor element 120.

As shown in FIG. 2, a shelf portion 111 protruding inward in a radial direction is formed on the inner side of the metal shell 110. Further, a cylindrical ceramic holder 113 made of alumina, a first powder packed bed 114 made of talc powder, a second powder packed bed 115 likewise made of talc powder, and the cylindrical ceramic sleeve 170 made of alumina are disposed in the metal shell 110 in this order from the leading end side toward the rear end side. Also, a cylindrical metal cup 116 integrated with the gas sensor element 120 together with the ceramic holder 113 and first powder packed bed 114 is disposed in the metal shell 110. Furthermore, a seal ring 117 is disposed between the ceramic sleeve 170 and a rear end portion 110k of the metal shell 110.

The ceramic holder 113 is disposed in the metal cup 116 and, on the leading end side of the ceramic holder 113, is engaged with the shelf portion 111 of the metal shell 110 via the metal cup 116. The gas sensor element 120 is inserted into the ceramic holder 113. Also, the whole of the first powder packed bed 114 is disposed in the metal cup 116. Furthermore, the airtightness between the metal shell 110 and gas sensor element 120 is secured by the presence of the second powder packed bed 115.

The ceramic sleeve 170 is a cylindrical body having a rectangular axial hole 170c along the axis AX. The ceramic sleeve 170 supports the gas sensor element 120 by having the plate-shaped gas sensor element 120 inserted in the rectangular axial hole 170c in the axis AX direction. The ceramic sleeve 170, after being mounted in the metal shell 110, is fixed in the metal shell 110 by bending the rear end portion 110k of the metal shell 110 inward in the radial direction, and crimped toward the rear end surface of the ceramic sleeve 170 via the seal ring 117.

A sensing portion 121 configured so as to be able to detect the concentration of oxygen in an exhaust gas is provided on the leading end side of the gas sensor element 120 disposedly fixed inside the metal shell 110. Furthermore, a porous protective layer 124 is formed on the leading end side of the gas sensor element 120 so as to cover the sensing portion 121. The porous protective layer 124 can suppress the attachment of water droplets or oil droplets entrained in an exhaust gas onto a detecting element 130 raised to a high temperature by heating with a heater element 160, described below. It is thus possible to prevent a crack from occurring in the gas sensor element 120.

Also, the leading end side of the gas sensor element 120 protrudes from the metal shell 110. Therefore, a double protector 101 of a bottomed cylindrical shape is fixed to the leading end side of the metal shell 110 by laser welding so as to cover the leading end side of the gas sensor element 120 protruding from the metal shell 110. A plurality of introduction holes 101c are formed in predetermined positions of the protector 101 so that an exhaust gas can be introduced into the inside of the protector 101 when the gas sensor 100 is disposed in an exhaust pipe.

The rear end side of the gas sensor element 120 protrudes from the metal shell 110 to the separator 181 side. On the rear end side of the gas sensor element 102, three sensor electrode pads in electrical continuity with the sensing portion 121; a pump cell electrode pad (an Ip electrode pad) 125, a COM electrode pad 126, and an electromotive force cell electrode pad (a Vs electrode pad) 127, are provided on the side of a first plate surface 122a, and two heater electrode pads 128 and 129 in electrical continuity with a heating resistor 163, described below, are provided on the side of a second plate surface 122c. The first plate surface 122a and second plate surface 122c correspond to a "first outer surface" of the invention.

The electrode pads 125, 126, 127, 128 and 129 of the gas sensor element 120 are connected to respective connection terminals 182, 183, 184, 185 and 186 inserted in the separator 181. Hereafter, a description will be given of this point. As shown in FIG. 2, a cylindrical metal pipe 103 is fixed to the rear end side of the metal shell 110 by laser welding, and the separator 181 is disposed on the inner side of the metal pipe 103. The three sensor connection terminals 182, 183 and 184 and two heater connection terminals 185 and 186 are disposed in the separator 181, and the sensor connection terminals 182, 183 and 184 and heater connection terminals 185 and 186 are housed in the separator 181 so as to be isolated and not in contact with one another.

The gas sensor element 120 protruding from the rear end side of the ceramic sleeve 170 is inserted in an opening 181c of the separator 181. Further, the sensor connection terminals 182, 183 and 184 are electrically connected in elastic contact to the sensor electrode pads 125, 126 and 127. Also, the heater connection terminals 185 and 186 are electrically connected in elastic contact to the heater electrode pads 128 and 129 of the gas sensor element 120. The enlarged view on the left side in FIG. 2 illustrates how the connection terminals 182, 183, 184, 185 and 186 are in contact with the electrode pads 125, 126, 127, 128 and 129 provided on the gas sensor element 120. The separator 181 is held in the metal pipe 103 such that the separator 181 is biased against a grommet 191, described below, by a substantially cylindrical biasing metal fixture 190 disposed around the separator 181.

The grommet 191, made of fluororubber, in which three sensor lead wires 193, 194 and 195 and two heater lead wires 196 and 197 are inserted, is disposed on the rear end side inner side of the metal pipe 103. The sensor lead wires 193, 194 and 195, the leading end sides of which are inserted in the separator 181 and crimped to the sensor connection terminals 182, 183 and 184, are electrically connected to the sensor connection terminals 182, 183 and 184. Also, the heater lead wires 196 and 197 as well, the leading end sides of which are inserted in the separator 181 and crimped to the heater connection terminals 185 and 186, are electrically connected to the heater connection terminals 185 and 186. The sensor lead wire 193 is connected to the Ip electrode pad 125 of the gas sensor element 120 via the sensor connection terminal 182, and the sensor lead wire 194 is connected to the COM electrode pad 126 of the gas sensor element 120 via the sensor connection terminal 183. Also, the sensor lead wire 195 is connected to the Vs electrode pad 127 of the gas sensor element 120 via the sensor connection terminal 184.

A2. Outline Configuration of Gas Sensor Element

Figure 3:
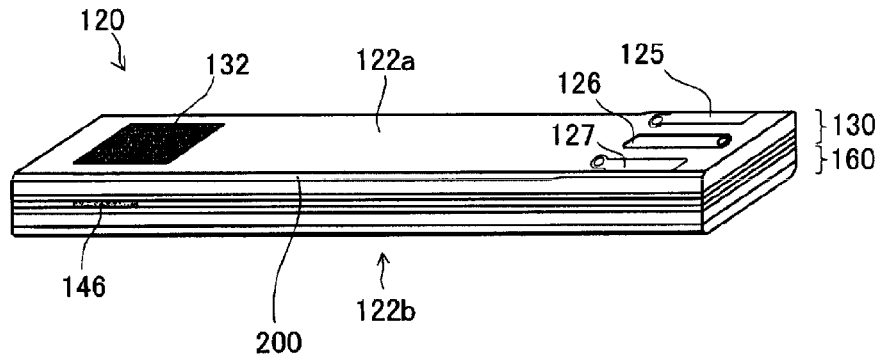
FIG. 3 is an illustration of a gas sensor element 120 before a protective layer 124 is formed.
Figure 4:
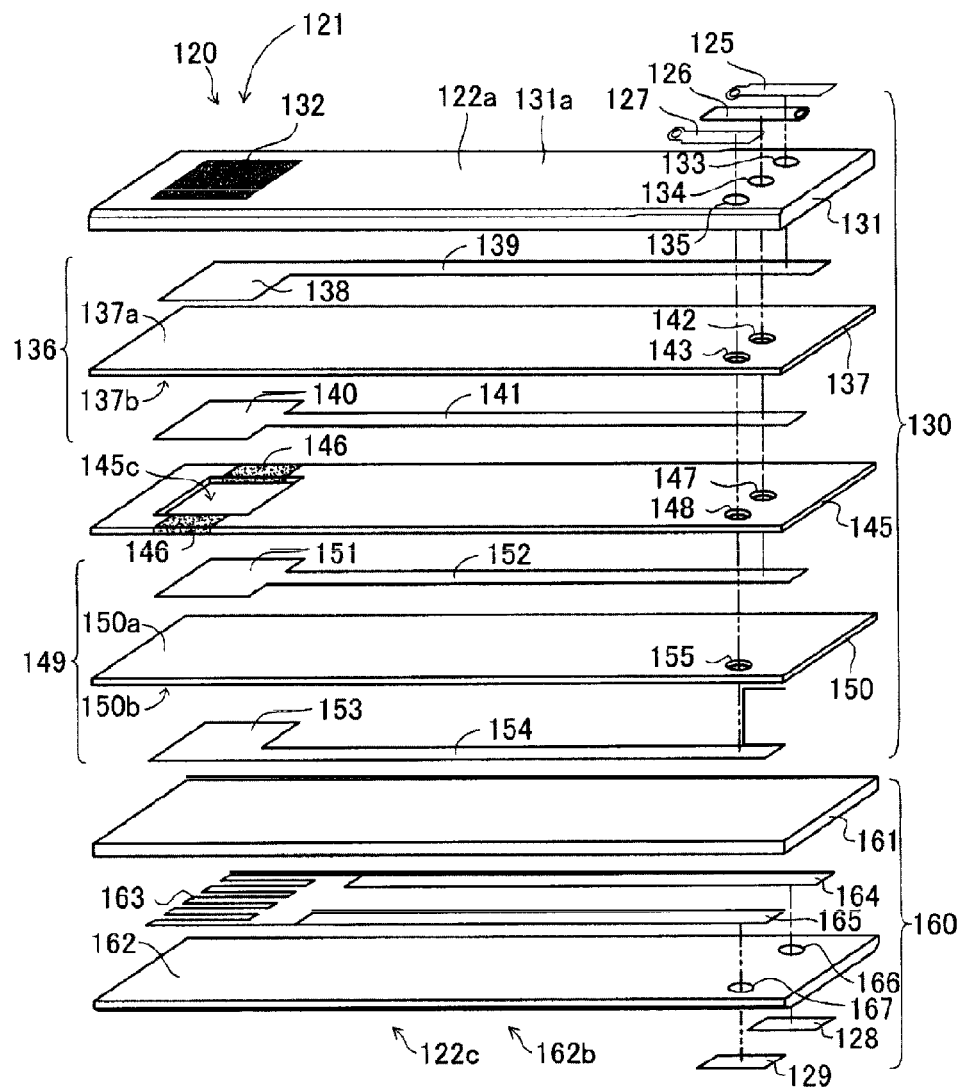
FIG. 4 is an illustration showing the gas sensor element 120 in exploded form.

FIG. 3 is an illustration showing the gas sensor element 120. FIG. 4 is an illustration showing the gas sensor element 120 in exploded form. In FIGS. 3 and 4, the protective layer 124 is omitted with the description of the gas sensor element 120 in mind. The gas sensor element 120 is configured by the plate-shaped detecting element 130, extending in the axial direction (in a left-right direction in FIG. 3), and the plate-shaped heater element 160, likewise extending in the axial direction, being stacked, fired and integrated. The left side in FIG. 3 corresponds to the leading end side in FIGS. 1 and 2, and the right side in FIG. 3 corresponds to the rear end side. The same also applies to FIG. 4, described below.

The detecting element 130 is such that the protective layer 131, a first solid electrolyte layer 137, a spacer 145, and a second solid electrolyte layer 150, each of which is plate-shaped, are stacked in this order from the first plate surface 122a side toward the second plate surface 122c side.

The protective layer 131 is made of alumina. A porous body 132 is formed on the leading end side of the protective layer 131. The Ip electrode pad 125, COM electrode pad 126, and Vs electrode pad 127 are formed in the rear end side vicinity on a first surface 131a of the protective layer 131 forming the first plate surface 122a of the gas sensor element 120, as the three sensor electrodes, so as to be aligned at predetermined intervals in a direction perpendicular to the axial direction (that is, in a width direction). The Ip electrode pad 125, COM electrode pad 126 and Vs electrode pad 127 are electrically connected respectively to three through hole conductors 133, 134 and 135 formed in the rear end side vicinity of the protective layer 131 so as to penetrate the protective layer 131, as shown by the broken lines in FIG. 4.

The first solid electrolyte layer 137 is made of zirconia, and two through hole conductors 142 and 143 are formed in the rear end side neighborhood so as to penetrate the first solid electrolyte layer 137. The through hole conductors 142 and 143 are electrically connected to the through hole conductors 134 and 135 formed in the protective layer 131 so as to penetrate the protective layer 131.

A Pt-based, porous, and rectangular first electrode portion 138 is formed on a first surface 137a (the upper side in FIG. 4) of the first solid electrolyte layer 137. The first electrode portion 138 is electrically connected, via a first lead portion 139, to the through hole conductor 133 formed in the protective layer 131 so as to penetrate the protective layer 131. Because of this, the first electrode portion 138 is in continuity with the Ip electrode pad 125 through the through hole conductor 133. The first electrode portion 138 is exposed to an exhaust gas through the porous body 132 provided in the protective layer 131.

A Pt-based, porous, and rectangular second electrode portion 140 is also formed on a second surface 137b (the lower side in FIG. 4) of the first solid electrolyte layer 137. The second electrode portion 140 is electrically connected, via a second lead portion 141, to the through hole conductor 142 formed in the first solid electrolyte layer 137 so as to penetrate the first solid electrolyte layer 137. Because of this, the second electrode portion 140 is in continuity with the COM electrode pad 126 through the through hole conductor 142 and through hole conductor 134. Further, the first solid electrolyte layer 137 and the paired first electrode portion 138 and second electrode portion 140 form a pump cell 136.

The spacer 145, made of alumina, has a rectangular opening on the leading end side thereof. The opening configures a gas detecting chamber 145c by the spacer 145 being stacked sandwiched between the first solid electrolyte layer 137 and second solid electrolyte layer 150. The second electrode portion 140 and a third electrode portion 151, described below, are exposed in the gas detecting chamber 145c. Furthermore, a diffusion controlling layer 146 that controls the rate of gas diffusion from the exterior into the gas detecting chamber 145c is formed in one portion of each side wall of the gas sensing chamber 145c. The diffusion controlling layers 146 are made of porous alumina. Two through hole conductors 147 and 148 are formed in the rear end side vicinity of the spacer 145 so as to penetrate the spacer 145. The through hole conductor 147 is electrically connected to the through hole conductor 142 formed in the first solid electrolyte layer 137. Also, the through hole conductor 148 is electrically connected to the through hole conductor 143 formed in the first solid electrolyte layer 137 so as to penetrate the first solid electrolyte layer 137.

The second solid electrolyte layer 150 is made of zirconia, and a through hole conductor 155 is formed in the rear end side vicinity so as to penetrate the second solid electrolyte layer 150. The through hole conductor 155 is electrically connected to the through hole conductor 148 formed in the spacer 145 so as to penetrate the spacer 145.

The Pt-based, porous, and rectangular third electrode portion 151 is formed on a first surface 150a (the upper side in FIG. 4) of the second solid electrolyte layer 150. The third electrode portion 151 is electrically connected, via a third lead portion 152, to the through hole conductor 147 formed in the spacer 145 so as to penetrate the spacer 145. Because of this, the third electrode portion 151 is in continuity with the COM electrode pad 126 through the through hole conductor 147, through hole conductor 142, and through hole conductor 134. That is, the third electrode portion 151 and second electrode portion 140 connected to the same COM electrode pad 126 are at the same electrical potential.

A Pt-based, porous, and rectangular fourth electrode portion 153 is also formed on a second surface 150b (the lower side in FIG. 4) of the second solid electrolyte layer 150. The fourth electrode portion 153 is electrically connected, via a fourth lead portion 154, to the through hole conductor 155 formed in the second solid electrolyte layer 150 so as to penetrate the second solid electrolyte layer 150. Because of this, the fourth electrode portion 153 is in continuity with the Vs electrode pad 127 through the through hole conductor 155, through hole conductor 148, through hole conductor 143, and through hole conductor 135. Further, the second solid electrolyte layer 150 and the paired third electrode portion 151 and fourth electrode portion 153 form an electromotive force cell 149. Also, the pump cell 136, electromotive force cell 149, and gas detecting chamber 145c configure the sensing portion 121.

The heater element 160 is configured by a first insulating layer 161 and second insulating layer 162, each of which is formed plate-shaped, being stacked in this order from the first plate surface 122a side toward the second plate surface 122c side. The first insulating layer 161 and second insulating layer 162 are made of alumina. The Pt-based heating resistor 163 of a serpentine shape is disposed on the leading end side between the first insulating layer 161 and second insulating layer 162, and heater lead portions 164 and 165 continuous one with each end of the heating resistor 163 extend to the rear end side.

Two through hole conductors 166 and 167 are formed in the rear end side vicinity of the second insulating layer 162 so as to penetrate the second insulating layer 162. Furthermore, the two heater electrode pads 128 and 129 are formed in the rear end side neighborhood on a second surface 162b of the second insulating layer 162 forming the second plate surface 122c of the gas sensor element 120 so as to be aligned in a direction perpendicular to the axial direction (that is, in the width direction of the gas sensor element 120). Of the two heater electrode pads, the heater electrode pad 128 is electrically connected to the heater lead portion 164 via the through hole conductor 166. Also, the heater electrode pad 129 is electrically connected to the heater lead portion 165 via the through hole conductor 167.

The gas sensor 100 configured in the way heretofore described is disposed in an exhaust pipe of an internal-combustion engine, and operates in the following way. Firstly, the heater element 160 is heated to several hundred degrees (for example, 700 to 800° C.) by a heater control circuit (not shown), thus activating the pump cell 136 and electromotive force cell 149. Furthermore, a minute current Icp (approximately 15 µA) is caused to flow to the electromotive force cell 149 through the Vs electrode pad 127, thus causing the fourth electrode portion 153 to function as an oxygen reference chamber. In this condition, when the atmosphere in the gas detecting chamber 145c is kept at a theoretical air-fuel ratio, a predetermined voltage (for example, 450 mV) is developed between the oxygen reference chamber in which the concentration of oxygen is kept substantially constant and the electromotive force cell 149. Therefore, a current Ip caused to flow to the pump cell 136 is timely adjusted using a predetermined electric circuit of a heretofore known configuration so that a voltage Vs of the electromotive force cell 149 is 450 mV to perform control for keeping the atmosphere in the gas detecting chamber 145c at the theoretical air-fuel ratio. By causing the gas sensor 100 to operate in this way, it is possible to measure the concentration of oxygen in an exhaust gas based on the value of the current Ip for keeping the inside of the gas detecting chamber 145c at the theoretical air-fuel ratio.

Returning to FIG. 3, the gas sensor element 120, extending in a longitudinal direction, has a chamfered portion 200 linking the first plate surface 122a of the gas sensor element 120, on which are disposed the electrode pads 125, 126 and 127, and a side surface 122b formed in a direction intersecting the first plate surface 122a. The gas sensor element 120 is such that after the individual layers are stacked one on another and fired, a longitudinal angular ridge formed between the first plate surface 122a and side surface 122b is chamfered. The angular ridge of the gas sensor element 120, in the first embodiment, means an angular portion formed between the first plate surface 122a and side surface 122b, and an angular portion formed between the second plate surface 122c and side surface 122b. A detailed description will next be given of the chamfered portion 200. In the first embodiment, the side surface 122b corresponds to the "second outer surface" of the invention.

A3. Chamfered Portion

FIGS. 5A and 5B illustrate the chamfered portion 200 of the gas sensor element 120 of the first embodiment. FIG. 5A is a plan view of the gas sensor element 120 seen from the first plate surface 122a side on which the electrode pads 125, 126 and 127 are disposed, and FIG. 5B is a side view of the gas sensor element 120. A fragmentary enlarged view of the chamfered portion 200 is shown together in each of FIGS. 5A and 5B. In FIGS. 5A and 5B, the lower side in the drawings (the sensing portion 121 side) refers to the leading end side of the gas sensor element 120, and the upper side in the drawings (the side of the electrode pads 125, 126 and 127) refers to the rear end side of the gas sensor element 120.

As shown in FIGS. 5A and 5B, the chamfered portion 200 has a leading end chamfered portion 210 formed in a leading end portion of the gas sensor element 120, a rear end chamfered portion 220 formed in a rear end portion of the gas sensor element 120, and an intermediate chamfered portion 230 formed between the leading end chamfered portion 210 and rear end chamfered portion 220 so as to link the leading end chamfered portion 210 and rear end chamfered portion 220. Also, a lower chamfered portion 250 chamfered at the same chamfer angle and in the same chamfer amount all along the longitudinal direction of the gas sensor element 120 is formed between the second plate surface 122c and side surface 122b of the gas sensor element 120. As used herein, the leading end portion means not only the vicinity of the leading end of the gas sensor element 120, but also a region including at least the sensing portion 121. In the same way, the rear end portion means not only the vicinity of the rear end of the gas sensor element 120, but also a region including at least the electrode pads 125, 126 and 127. The intermediate chamfered portion 230 does not refer to the vicinity of the center of the gas sensor element 120, but means a portion between the leading end chamfered portion 210 and rear end chamfered portion 220.

The intermediate chamfered portion 230 is formed so as to be positioned closer to the rear end side in the longitudinal direction than a rear end position HP of the heating resistor 163 of the heater element 160. Also, the intermediate chamfered portion 230 is formed so as to be positioned closer to the rear end side in the longitudinal direction than a leading end position SP of the separator 181.

The electrode pads 125 and 127 are each disposed adjacent to the rear end chamfered portion 220. As used herein, "being disposed adjacent" means a condition in which no other member or space exists between the rear end chamfered portion 220 and each electrode pad 125 and 127. In other words, "being disposed adjacent" means that an end portion of each electrode pad 125 and 127 is positioned in a boundary portion between the rear end chamfered portion 220 and first plate surface 122a.

Figure 6A:
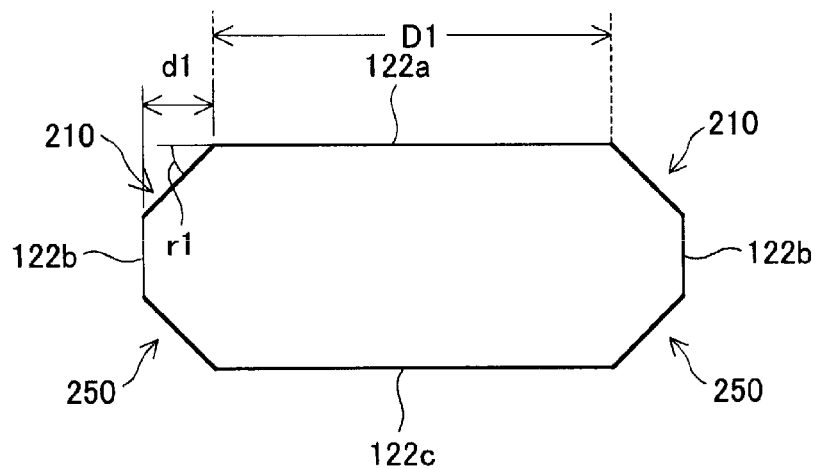
FIGS. 6A to 6C are sectional views of the gas sensor element 120 of the first embodiment.
Figure 6B:
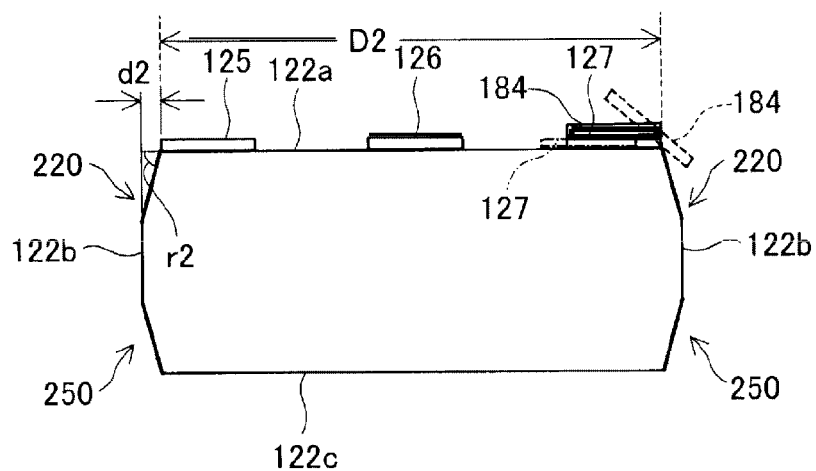
Figure 6C:
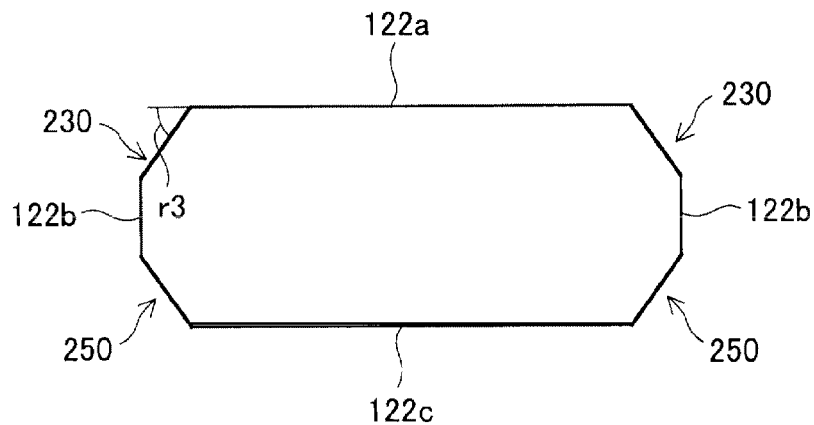

FIGS. 6A to 6C are sectional views of the gas sensor element 120 in the first embodiment. In FIGS. 6A to 6C, the illustration of internal components of the gas sensor element 120, such as the first solid electrolyte layer 137, spacer 145, and second solid electrolyte layer 150, in each sectional view will be omitted in order to simplify the description.

FIG. 6A is a sectional view of the leading end chamfered portion 210 in section A-A of FIG. 5A. As shown in FIG. 6A, the leading end chamfered portion 210 is chamfered at a chamfer angle r1 and chamfer length d1 with respect to the first plate surface 122a. In the first embodiment, the chamfer angle r1 is 45°, and the chamfer length d1 is 0.3 mm. Two leading end chamfered portions 210 are formed one between the first plate surface 122a and each side surface 122b.

FIG. 6B is a sectional view of the rear end chamfered portion 220 in section B-B of FIG. 5A. A chamfer angle r2 of the rear end chamfered portions 220 to the first plate surface 122a is formed so as to be larger than the chamfer angle r1 of the leading end chamfered portion 210 to the first plate surface 122a. In the first embodiment, the chamfer angle r2 is 75°. The chamfer angle r2 is preferably 75° or less, and is larger than the chamfer angle r1. Because the chamfer angle r2 is larger than the chamfer angle r1 of the leading end chamfered portion 210, a chamfer amount d2 of the rear end chamfered portion 220 becomes smaller than d1.

By configuring the chamfered portions in this way, it is possible to increase the area of the first plate surface 122a (a width D1 of the first plate surface 122a) in the rear end portion of the gas sensor element 120 as compared with the area of the first plate surface 122a (a width D2 of the first plate surface 122a) in the leading end portion, thus eliminating the need to shorten the distances between the electrode pads 125, 126 and 127. Further, it is possible to form sufficient spaces between the electrode pads 125, 126 and 127 in order to secure adequate insulating properties. Also, it is not necessary to secure the distances between the electrode pads 125, 126 and 127 by reducing the area of the electrode pads 125, 126 and 127, and it is possible to secure the contactability between the electrode pads 125, 126 and 127 and connection terminals 182, 183 and 184. Furthermore, because the chamfer angle r1 of the leading end chamfered portion 210 is made smaller than the chamfer angle r2 of the rear end chamfered portion 220, it is possible to adequately secure the size (chamfer amount d1) of the leading end chamfered portion 210, and it is possible to adequately maintain the thermal shock resistance of the leading end portion of the gas sensor element 120 that is exposed to an exhaust gas.

Also, because the electrode pads 125 and 127 are each disposed so as to be adjacent to the rear end chamfered portion 220, it is possible to secure electrical continuity, for example, even when a displacement or inclination of the connection terminal 184 occurs, as shown by the broken line in FIG. 6B. When a displacement or incline of the connection terminal 184 occurs, for example, when the electrode pad 127 is disposed so as not to be adjacent to the rear end chamfered portion 220, as shown by the chain line in FIG. 6B, the electrical continuity of the electrode pad 127 and connection terminal 184 is not secured. Also, it is not necessary to secure the distances between the electrode pads 125, 126 and 127 by reducing the area of the electrode pads 125, 126 and 127, and it is possible to secure the contactability between the electrode pads 125, 126 and 127 and connection terminals 182, 183 and 184. Furthermore, because the chamfer angle r1 of the leading end chamfered portion 210 is made smaller than the chamfer angle r2 of the rear end chamfered portion 220, it is possible to adequately secure the size (chamfer amount d1) of the leading end chamfered portion 210, and it is possible to adequately maintain the thermal shock resistance of the leading end portion of the gas sensor element 120 that is exposed to an exhaust gas.

FIG. 6C is a sectional view of the intermediate chamfered portion 230 in section C-C of FIG. 5A. The intermediate chamfered portion 230 is chamfered at a chamfer angle r3 equal to or larger than the chamfer angle r1 (45°) of the leading end chamfered portion 210 and equal to or smaller than the chamfer angle r2 (75°) of the rear end chamfered portion 220. The intermediate chamfered portion 230 is formed so that the chamfer angle r3 increases gradually from the leading end side toward the rear end side. By so doing, the leading end chamfered portion 210 and rear end chamfered portion 220 are linked together with a smooth plane by the intermediate chamfered portion 230.

As shown in FIGS. 6A to 6C, two lower chamfered portions 250 are formed one between the second plate surface 122c and each side surface 122b. The chamfer angle and chamfer length of the lower chamfered portion 250 are 45° and 0.3 mm, respectively, which are the same as those of the leading end chamfered portion 210.

A4. Manufacturing Process

Figure 7:
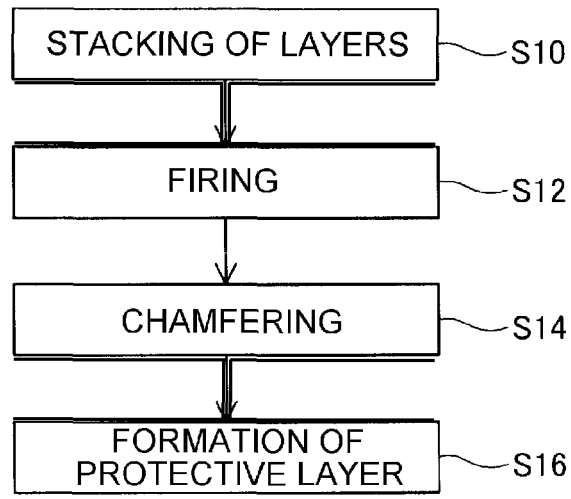
FIG. 7 illustrates a process of manufacturing the gas sensor 100 of the first embodiment.

A description will be given, referring to FIGS. 7 to 9B, of a process of manufacturing the gas sensor 100. FIG. 7 illustrates a process of manufacturing the gas sensor 100 of the first embodiment.

Firstly, in accordance with a heretofore known method, the detecting element 130 and heater element 160 configuring the gas sensor element 120 are stacked in the order shown in FIG.

4 and press-laminated (step S10), and the laminated body is fired (step S12). The firing temperature is, for example, 1500° C.

Next, the angular ridge of the fired gas sensor element 120 is chamfered (step S14). In the first embodiment, the angular ridge of the gas sensor element 120 is cut by a grindstone.

Figure 8:
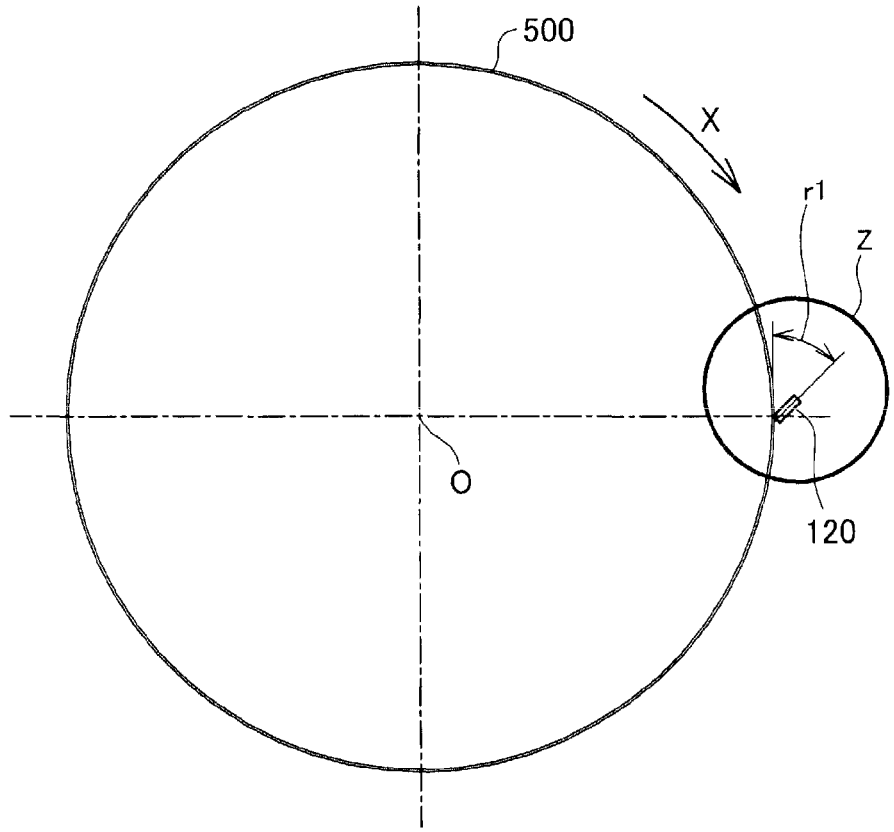
FIG. 8 illustrates a chamfering method in step S14.
Figure 9A:
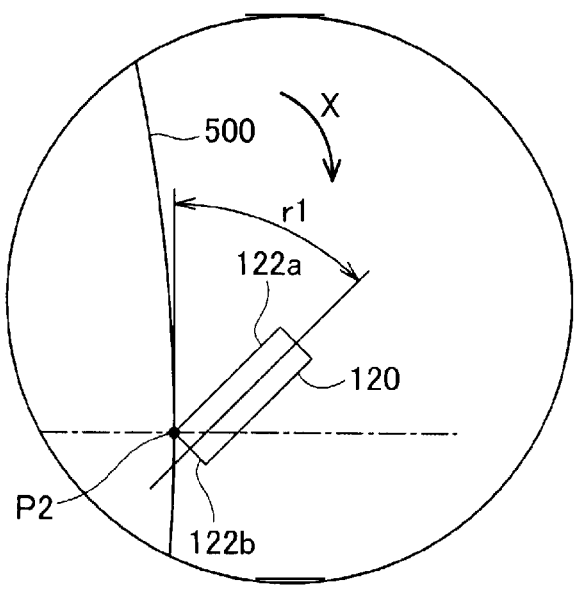
FIGS. 9A and 9B are fragmentary enlarged views of the chamfering method shown in FIG. 8.
Figure 9B:
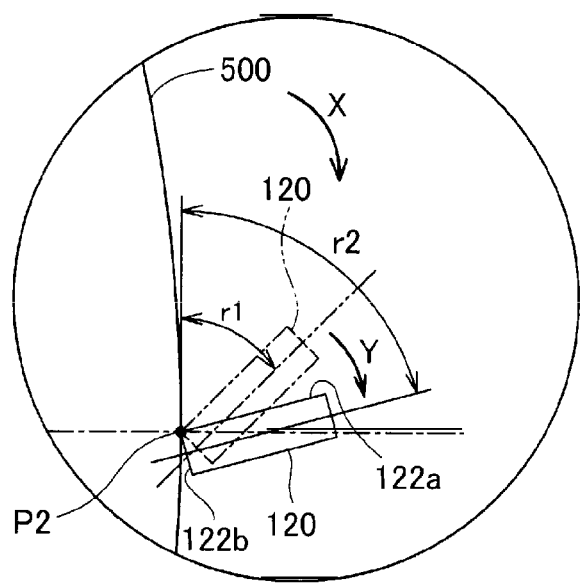

FIG. 8 illustrates a chamfering method of step S14. FIGS. 9A and 9B are fragmentary enlarged views of a circle Z in FIG. 8. FIG. 9A illustrates a process of forming the leading end chamfered portion 210 of the gas sensor element 120. FIG. 9B illustrates a process of forming the intermediate chamfered portion 230 and rear end chamfered portion 220 after the formation of the leading end chamfered portion 210. As shown in FIGS. 8 to 9B, a grindstone 500 that, by rotating in an arrow X direction, cuts a contact portion of an object to be cut is utilized in the chamfering step.

A description will be given of the formation of the leading end chamfered portion 210. The gas sensor element 120 is brought close to the grindstone 500 so that the longitudinal direction of the gas sensor element 120 is parallel to the direction of a rotation axis O of the grindstone 500, as shown in FIGS. 8 and 9A. At this time, an angular ridge P2 of the gas sensor element 120 is abutted against the grindstone 500 in a condition in which the first plate surface 122a of the gas sensor element 120 is tilted at the chamfer angle r1 (45°) to a cutting surface 510 of the grindstone 500. Further, the angular ridge P2 of the gas sensor element 120 is chamfered in the longitudinal direction by horizontally moving the gas sensor element 120 in the direction of the rotation axis O of the grindstone 500 with the gas sensor element 120 remaining abutted against the grindstone 500. By so doing, the leading end chamfered portion 210 chamfered at the chamfer angle r1 (45°) is formed. When cutting, the gas sensor element 120 may be held by a holding jig, or may be held by an operator. Also, the cutting step may be carried out by a cutting device wherein the holding jig holding the gas sensor element 120 can be moved in the longitudinal direction and a Y direction, described below.

When formation of the leading end chamfered portion 210 is finished, formation of the intermediate chamfered portion 230 and rear end chamfered portion 220 is continuously carried out.

In FIG. 9B, the gas sensor element 120 shown by the broken line is the gas sensor element 120 in FIG. 9A. When the leading end chamfered portion 210 is finished, the gas sensor element 120 is rotated in the Y direction with the angular ridge P2 as an axis while being horizontally moved in the direction of the rotation axis O of the grindstone 500. This is done in a condition in which the angular ridge P2 of the gas sensor element 120 is abutted against the grindstone 500, as shown in FIG. 9B, thus gradually changing the angle (chamfer angle) of the first plate surface 122a from the chamfer angle r1 (45°) to the chamfer angle r2 (75°) of the rear end chamfered portion 220. When changing the chamfer angle, the rotation speed of the grindstone 500, a drag between the gas sensor element 120 and grindstone 500, and a time for which the gas sensor element 120 is abutted against the grindstone 500 are adjusted so that the rate of increase in the chamfer angle is substantially uniform from the rear end side end portion of the leading end chamfered portion 210 to a position forming the leading end side end portion of the rear end chamfered portion 220. By so doing, the intermediate chamfered portion 230 is formed so that the chamfer angle is equal to or larger than the chamfer angle r1 and equal to or smaller than the chamfer angle r2, and increases gradually from the leading end side toward the rear end side.

The rear end chamfered portion 220 is formed in the same way as the leading end chamfered portion 210, except that the chamfer angles are different from one another. That is, after forming the intermediate chamfered portion 230, the gas sensor element 120 is horizontally moved in the direction of the rotation axis O of the grindstone 500 with the gas sensor element 120 remaining abutted against the grindstone 500. This is done in a condition in which the angle of the first plate surface 122a to the cutting surface 510 of the grindstone 500 is the chamfer angle r2 (75°), as shown in FIG. 9B. By so doing, the angular ridge P2 in the vicinity of the rear end of the gas sensor element 120 is chamfered in the longitudinal direction, and the rear end chamfered portion 220 chamfered at the chamfer angle r2 (75°) is formed.

The chamfer amount of the chamfered portion 200 of the gas sensor element 120 can be adjusted in accordance with the rotation speed of the grindstone 500, a drag between the gas sensor element 120 and grindstone 500, and a time for which the gas sensor element 120 is abutted against the grindstone 500, and is appropriately adjusted so as to obtain a desired chamfer amount.

The description will now be continued with reference to FIG. 7. The protective layer 124 is formed in the leading end portion of the gas sensor element 120 on which are formed the chamfered portions 200 so as to cover the sensing portion 121 (step S16). The gas sensor element 120 is manufactured, as heretofore described. The manufactured gas sensor element 120 is assembled with the metal shell 110, separator 181, and metal pipe 103, to thereby manufacture the gas sensor 100.

In the first embodiment, the gas sensor element 120 applied to the gas sensor 100 for measuring the concentration of an oxygen gas is illustrated, but it goes without saying that the configuration of the chamfered portion 200 can be applied to a gas sensor element for measuring the concentration of not only an oxygen gas, but various kinds of gases.

A5. Test Results

Test results from carrying out a withstand voltage test on the gas sensor element 120 are shown in Table 1 below. The withstand voltage test was carried out in accordance with the following process. In the test, the chamfer amount of the chamfered portion is provided so as to be uniform at 0.2 mm in the longitudinal direction of the gas sensor element 120.

1. An application of a predetermined voltage to the heater element 160 and a suspension of the application are taken to be one cycle, and the cycle is repeated ten times, thus confirming whether or not a crack (or a chipping) has occurred in the gas sensor element 120.

2. If no crack has occurred in the gas sensor element 120, a voltage value is increased, and the process 1 is repeated until a crack occurs.

Test results in Table 1 are as follows.
OK: No crack has occurred.
NG: A crack has occurred.

TABLE 1

| Chamfer | Withstand Voltage Test | | | | | | | |
|---|---|---|---|---|---|---|---|---|
| Angle | 12 V | 13 V | 14 V | 15 V | 16 V | 17 V | 18 V | 19 V |
| 20° | OK | OK | OK | NG | | | | |
| 30° | OK | OK | OK | OK | OK | OK | OK | NG |
| 45° | OK | OK | OK | OK | OK | OK | OK | NG |
| 60° | OK | OK | OK | OK | OK | OK | OK | NG |
| 70° | OK | OK | OK | OK | OK | OK | OK | NG |
| 80° | OK | OK | OK | OK | OK | NG | | |

As shown in Table 1, in the case of a range of 30° chamfer angle, no crack occurred until a voltage on the order of 18 V was reached, and it was possible to adequately maintain the thermal shock resistance of the gas sensor element 120. Meanwhile, in the case of a chamfer angle of 20° or less, a crack could occur in the gas sensor element 120 at a low applied voltage of 15 V, and the thermal shock resistance could not be adequately maintained. Also, in the case of a chamfer angle of 80° or more, a crack occurred in the leading end portion of the gas sensor element 120 at an applied voltage of 17 V. In this case, the crack occurred because of the shortened distance between the heating resistor 163 provided in the leading end portion of the gas sensor element 120 and each chamfered portion forming the outer side surface. Therefore, the chamfer angle r1 of the leading end chamfered portions 210 is more preferably 30 to 70°.

The heretofore described gas sensor element 120 of the first embodiment is such that the chamfered portion 200 chamfered all along the longitudinal direction of the gas sensor element is formed between the first plate surface 122a and side surface 122b. Consequently, it is possible to suppress damage, such as a chipping or cracking, to the gas sensor element 120. Also, the chamfered portion 200 of the gas sensor element 120 is such that the chamfer angle r2 of the rear end chamfered portion 220 formed in the rear end portion in which the electrode pad 125 is disposed is larger than the chamfer angle r1 of the leading end chamfered portion 210 formed in the leading end portion in which the sensing portion 121 is provided. Consequently, it is possible to increase the area of the first plate surface 122a in the rear end portion of the gas sensor element 120 as compared with the area of the first plate surface 122a in the leading end portion. Also, it is not necessary to shorten the distances between the electrode pads 125, 126 and 127, and it is possible to secure the insulating properties between the plurality of electrode pads 125, 126 and 127. Also, it is not necessary to secure the distances between the electrode pads 125, 126 and 127 by reducing the area of the electrode pads 125, 126 and 127, and it is possible to secure the contactability between the electrode pads 125, 126 and 127 and connection terminals 182, 183 and 184. Furthermore, as the chamfer angle r1 of the leading end chamfered portion 210 is made smaller than the chamfer angle r2 of the rear end chamfered portion 220, it is possible to adequately secure the size (chamfer amount d1) of the leading end chamfered portion 210, and it is possible to adequately maintain the thermal shock resistance of the leading end portion of the gas sensor element 120 exposed to an exhaust gas.

Also, the electrode pads 125 and 127 are each provided so as to be adjacent to the chamfered portion 200. By so doing, it is possible to secure the contactability between the electrode pads 125, 126 and 127 and connection terminals 182, 183 and 184, with high accuracy, even when a displacement occurs in the positions of the connection terminals 182, 183 and 184 relative to the gas sensor element 120. Also, it is not necessary to secure the distances between the electrode pads 125, 126 and 127 by reducing the area of the electrode pads 125, 126 and 127, and it is possible to secure the contactability between the electrode pads 125, 126 and 127 and connection terminals 182, 183 and 184. Furthermore, as the chamfer angle r1 of the leading end chamfered portion 210 is made smaller than the chamfer angle r2 of the rear end chamfered portion 220, it is possible to adequately secure the size (chamfer amount d1) of the leading end chamfered portion 210, and it is possible to adequately maintain the thermal shock resistance of the leading end portion of the gas sensor element 120 exposed to an exhaust gas.

Also, according to the gas sensor element 120 of the first embodiment, the chamfered portion 200 is chamfered at a chamfer angle of 30° or more. Consequently, it is possible to adequately maintain the thermal shock resistance of the gas sensor element 120 on account of the chamfering.

Also, according to the gas sensor 100 of the first embodiment, the intermediate chamfered portion 230 chamfered at a chamfer angle equal to or larger than the chamfer angle r1 of the leading end chamfered portion 210 and equal to or smaller than the chamfer angle r3 of the rear end chamfered portion 220 is formed between the rear end chamfered portion 220 and leading end chamfered portion 210 of the gas sensor element 120. Consequently, it is possible to reduce the difference in chamfer angle between the rear end chamfered portion 220 and leading end chamfered portion 210 without producing a step in the boundary portion between the rear end chamfered portion 220 and leading end chamfered portion 210. Also, it is possible to suppress damage to the boundary portion due to a shock from the exterior.

According to the gas sensor 100 of the first embodiment, the intermediate chamfered portion 230 of the gas sensor element 120 is formed so as to be positioned closer to the rear end side in the longitudinal direction than the leading end position of the separator 181. Consequently, because the leading end chamfered portion 210 having a chamfer angle larger than those of the intermediate chamfered portion 230 and rear end chamfered portion 220 is formed in an exposed portion of the gas sensor element 120 not covered with the separator 181, it is possible to suppress damage to the exposed portion of the gas sensor element 120.

According to the gas sensor 100 of the first embodiment, the intermediate chamfered portion 230 of the gas sensor element 120 is formed so as to be positioned closer to the rear end side in the longitudinal direction than the rear end position of the heat resistor 163. Consequently, because the leading end chamfered portion 210 having a chamfer angle larger than those of the intermediate chamfered portion 230 and rear end chamfered portion 220 is formed in the leading end portion in which the heat resistor 163 is provided, it is possible to adequately maintain the thermal shock resistance of the leading end portion of the gas sensor element 120 even when the leading end portion is affected by heat from the heat resistor 163.

According to the gas sensor 100 of the first embodiment, the intermediate chamfered portion 230 of the gas sensor element 120 is formed so that the chamfer angle r2 increases from the leading end side toward the rear end side in the longitudinal direction. Consequently, it is possible to prevent a ridge portion from being formed between the rear end chamfered portion 220 and leading end chamfered portion 210, and it is possible to suppress damage to the boundary portion between the rear end chamfered portion 220 and leading end chamfered portion 210.

According to the gas sensor 100 of the first embodiment, the chamfer length of the chamfered portion 200 is 0.1 mm or more. Consequently, it is possible to adequately secure the thermal shock resistance of the gas sensor element 120.

B. SECOND EMBODIMENT

In a second embodiment, the chamfer amount is adjusted to form the leading end chamfered portion, intermediate chamfered portion, and rear end chamfered portion of a gas sensor element. In the second embodiment, components including configurations the same as those of the first embodiment are given the same reference numerals and symbols.

B1. Configuration of Gas Sensor Element

FIG. 10A is a plan view of a gas sensor element 320 seen from the side of a first plate surface 322a on which the electrode pads 125, 126, and 127 are disposed, and FIG. 10B is a side view of the gas sensor element 320. A fragmentary enlarged view of a chamfered portion 400 is shown together with each of FIGS. 10A and 10B.

As shown in FIGS. 10A and 10B, the chamfered portion 400 of the gas sensor element 320, in the same way as the gas sensor element 120 of the first embodiment, includes a leading end chamfered portion 410 formed in a leading end portion of the gas sensor element 320, a rear end chamfered portion 420 formed in a rear end portion of the gas sensor element 320, and an intermediate chamfered portion 430 formed between the leading end chamfered portion 410 and rear end chamfered portion 420 so as to link the leading end chamfered portion 410 and rear end chamfered portion 420. Also, the lower chamfered portion 250 chamfered at the same chamfer angle and in the same chamfer amount all along a longitudinal direction of the gas sensor element 320 is formed between a second plate surface 322c and side surface 322b of the gas sensor element 320. The electrode pads 125 and 127 are each disposed adjacent to the rear end chamfered portion 420.

The intermediate chamfered portion 430 is chamfered in a chamfer amount equal to or larger than the chamfer amount of the rear end chamfered portion 420 and equal to or smaller than the chamfer amount of the leading end chamfered portion 210 so that the chamfer amount decreases gradually toward the rear end side. That is, the leading end chamfered portion 210 and rear end chamfered portion 220 are linked together with a smooth plane by the intermediate chamfered portion 230.

Figure 11A:
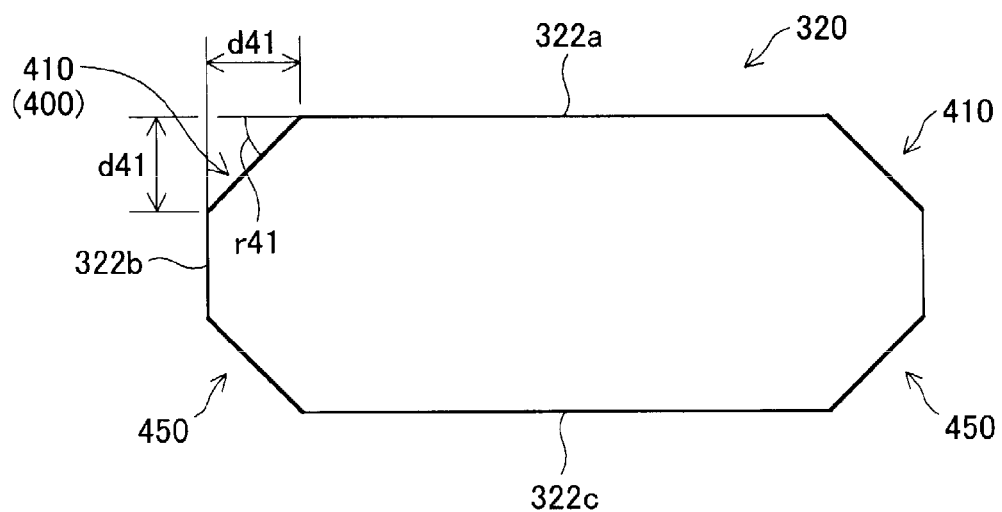
FIGS. 11A and 11B are sectional views of the gas sensor element 320 of the second embodiment.
Figure 11B:
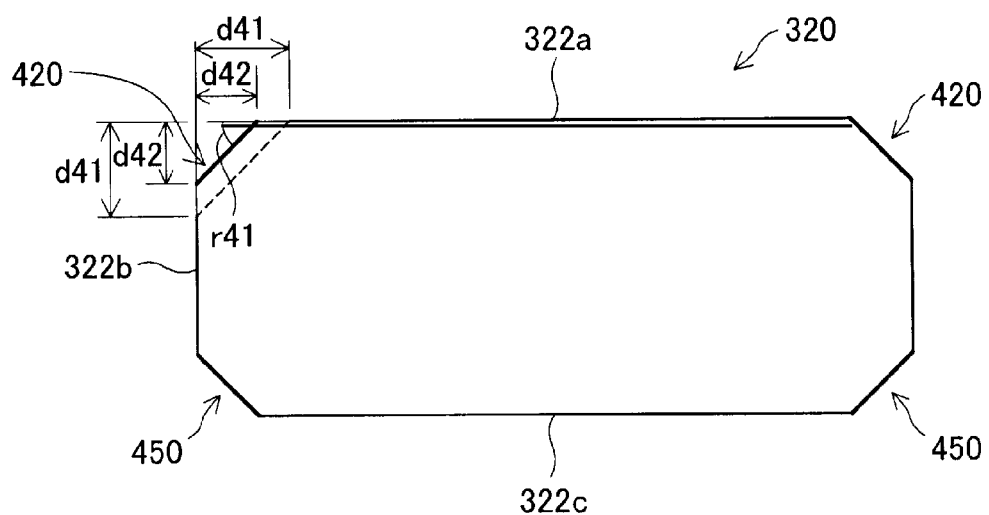

FIGS. 11A and 11B are sectional views of the gas sensor element 320 of the second embodiment. In FIGS. 11A and 11B, the illustration of internal components of the gas sensor element 320, such as the first solid electrolyte layer 137, spacer 145, and second solid electrolyte layer 150, in each sectional view will be omitted in order to simplify the description.

FIG. 11A is a sectional view of the leading end chamfered portion 410 in section D-D of FIG. 10A. As shown in FIG. 11A, the leading end chamfered portion 410 is chamfered in a chamfer amount d41 and at a chamfer angle r41 with respect to the first plate surface 322a. In the second embodiment, the chamfer amount d41 is 0.3 mm, and the chamfer angle r41 is 45°. Two leading end chamfered portions 410 are formed, including one between the first plate surface 322a and each side surface 322b.

FIG. 11B is a sectional view of the rear end chamfered portion 420 in section E-E of FIG. 10A. As shown in FIG. 11B, the rear end chamfered portion 420 is chamfered in a chamfer amount d42 smaller than the chamfer amount d41 of the leading end chamfered portion 410 and at the chamfer angle r41. In the second embodiment, the chamfer amount d42 is 0.1 mm, and the chamfer angle r41 is 45°. The chamfer amount d42 is preferably 0.1 mm or more, and is smaller than the chamfer amount d41. Two rear end chamfered portions 420 are formed, including one between the first plate surface 322a and each side surface 322b.

The intermediate chamfered portion 430, although not illustrated, is chamfered in a chamfer amount smaller than the chamfer amount d41 of the leading end chamfered portion 410 and larger than the chamfer amount d42 of the rear end chamfered portion 420. The intermediate chamfered portion 430 is formed so that the chamfer amount increases gradually from the leading end side toward the rear end side. The chamfer angle of the intermediate chamfered portion 430 is r1 (45°) which is the same as that of the leading end chamfered portion 410.

Also, as shown in FIGS. 11A and 11B, two lower chamfered portions 450 are formed, including one between the second plate surface 322c and each side surface 322b. The chamfer angle and chamfer length of the lower chamfered portion 450 are 45° and 0.3 mm respectively which are the same as those of the leading end chamfered portion 410.

B2. Test Results

Test results from carrying out a withstand voltage test on the gas sensor element 320 of the second embodiment are shown in Table 2 below. The withstand voltage test was carried out in accordance with the same process as that of the test in the first embodiment.

Test results are as follows.
OK: No crack has occurred.
NG: A crack has occurred.

TABLE 2

| Chamfer | Withstand Voltage Test | | | | | | | |
|---------|------|------|------|------|------|------|------|------|
| Amount  | 12 V | 13 V | 14 V | 15 V | 16 V | 17 V | 18 V | 19 V |
| 0.03    | OK   | OK   | NG   |      |      |      |      |      |
| 0.1     | OK   | OK   | OK   | OK   | OK   | OK   | OK   | NG   |
| 0.2     | OK   | OK   | OK   | OK   | OK   | OK   | OK   | NG   |
| 0.3     | OK   | OK   | OK   | OK   | OK   | OK   | OK   | NG   |
| 0.4     | OK   | OK   | OK   | OK   | OK   | NG   |      |      |

As shown in Table 2, in the case of a range of 0.1≤chamfer amount, no crack occurred until a voltage on the order of 18 V was reached, and it was possible to adequately maintain the thermal shock resistance of the gas sensor element 320. Meanwhile, in the case of a chamfer amount of 0.3 mm or less, a crack could occur in the gas sensor element 320 at a low applied voltage of 14 V, and the thermal shock resistance could not be adequately maintained. Also, in the case of a chamfer amount of 0.4 mm or more, a crack occurred in the leading end portion of the gas sensor element 320 when at an applied voltage of 17 V. In this case, the crack occurred because of the shortened distance between the heating resistor 163 provided in the leading end portion of the gas sensor element 320 and each chamfered portion forming the outer side surface. Therefore, the chamfer angle r41 of the leading end chamfered portions 410 is more preferably 30 to 70°.

According to the gas sensor element 320 of the second embodiment, the chamfered portion 400 chamfered all along the longitudinal direction of the gas sensor element is formed between the first plate surface 322a and side surface 322b. Consequently, it is possible to suppress damage, such as a chipping or cracking, to the gas sensor element 320. Also, the chamfered portion 400 of the gas sensor element 320 is such that the chamfer length d42 of the rear end chamfered portion 420 formed in the rear end portion in which the electrode pads 125, 126 and 127 are disposed is shorter than the chamfer length d41 of the leading end chamfered portion 410 formed in the leading end portion in which the sensing portion 121 is provided. Consequently, it is possible to increase the area of the first plate surface 322a in the rear end portion of the gas sensor element 320 as compared with the area of the first plate surface 322a in the leading end portion. As such, it is not necessary to shorten the distances between the electrode pads 125, 126 and 127, and it is possible to secure the insulating properties between the plurality of electrode pads 125, 126 and 127. Also, it is not necessary to secure the distances between the electrode pads 125, 126 and 127 by reducing the area of the electrode pads 125, 126 and 127, and it is possible to secure the contactability between the electrode pads 125, 126 and 127 and connection terminals 182, 183 and 184. Furthermore, as the chamfer length d41 of the leading end chamfered portion 410 is made larger than the chamfer length d42 of the rear end chamfered portion 420, it is possible to adequately secure the size of the leading end chamfered portion 410. Also, it is possible to adequately maintain the thermal shock resistance of the leading end portion of the gas sensor element 320 exposed to an exhaust gas.

Also, the electrode pads 125 and 127 are each provided so as to be adjacent to the chamfered portion 400. By so doing, it is possible to secure the contactability between the electrode pads 125, 126 and 127 and connection terminals 182, 183 and 184, with high accuracy, even when a displacement occurs in the positions of the connection terminals 182, 183 and 184 relative to the gas sensor element 320. Also, it is possible to increase the area of the electrode pads 125, 126 and 127 to the maximum possible without shortening the distances between the electrode pads 125, 126 and 127. Also, it is possible to secure the contactability between the electrode pads 125, 126 and 127 and connection terminals 182, 183 and 184 while securing the insulating properties between the plurality of electrode pads 125, 126 and 127.

According to the gas sensor element 320 of the second embodiment, the chamfer length of the chamfered portion 400 is 0.1 mm or more. Consequently, it is possible to adequately maintain the thermal shock resistance of the gas sensor element 320.

According to the gas sensor element 320 of the second embodiment, the chamfered portion is chamfered at a chamfer angle of 30° or more. Consequently, it is possible to adequately maintain the thermal shock resistance of the gas sensor element 320.

C. MODIFICATION EXAMPLES

C1. Modification Example 1

The chamfered portion 200, 400 is formed all along the longitudinal direction of the gas sensor element 120, 320. However, the embodiment may be modified to have, for example, a configuration wherein the leading end chamfered portion 210, 410 is formed in the leading end portion of the gas sensor element 120; the rear end chamfered portion 220, 420 chamfered at a chamfer angle larger than the chamfer angle of the leading end chamfered portion 210, 410 or in a chamfer amount smaller than the chamfer amount of the leading end chamfered portion 210, 410 is formed in the rear end portion of the gas sensor element 120; and a portion between the leading end chamfered portion 210, 410 and rear end chamfered portion 220, 420 is not chamfered. In other words, a configuration may be adopted wherein no intermediate chamfered portion 230, 430 is formed. This is because as the central portion of the gas sensor element 120 is disposed inside the metal shell 110, breakage due to chipping or cracking is unlikely to occur.

C2. Modification Example 2

Also, in the embodiment, the intermediate chamfered portion 230, 430 is disposed closer to the rear end side than the leading end position SP of the separator 181 but, for example, may be provided in a position closer to the rear end side than the rear end position HP of the heat resistor 163 and closer to the leading end side than the leading end leading end position SP, or may be provided in a position closer to the leading end side than the rear end position HP of the heat resistor 181. In the invention, the leading end chamfered portion 210, 410 is provided in the leading end portion in which the sensing portion 121 is provided, and the rear end chamfered portion 220, 420 is provided in the rear end portion in which the electrode pads 125, 126 and 127 are provided. Therefore, the intermediate chamfered portion 230, 430 may be provided throughout a portion between the leading end chamfered portion 210, 410 and rear end chamfered portion 220, 420 (that is, from a portion closer to the leading end side than the rear end position HP to a portion closer to the rear end side than the rear end position HP).

C3. Modification Example 3

In the embodiment, the lower chamfered portion 250, 450 is chamfered at the same chamfer angle and in the same chamfer amount all along the longitudinal direction of the gas sensor element 120, 320. However, the embodiment may be modified, for example, such that a lower leading end chamfered portion, a lower rear end chamfered portion, and a lower intermediate chamfered portion are formed in the same way as the chamfered portion 200, 400. Also, in this case, the leading end chamfered portion 210, 410, rear end chamfered portion 220, 420, and intermediate chamfered portion 230, 430 of the chamfered portion 200, 400 may be the same in size as, or may be different in size from, the respective lower leading end chamfered portion, lower rear end chamfered portion, and lower intermediate chamfered portion of the lower chamfered portion.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2012-049294 filed Mar. 6, 2012, the disclosure of which is incorporated herein by reference in its entirety.

What is claimed is:
1. A gas sensor, comprising:
a gas sensor element including a plate-shaped detecting element extending in a longitudinal direction, a sensing portion, disposed in a leading end portion in the longitudinal direction of the detecting element and detecting a specified gas in a gas to be measured, and a plurality of electrode pads disposed on an outer surface in a rear end portion in the longitudinal direction of the detecting element, at least one of the electrode pads outputting a detection signal from the sensing portion to an external circuit; and
a housing that encloses the periphery of the gas sensor element, wherein
the gas sensor element has at least one chamfered portion linking a first outer surface and a second outer surface of the detecting element, the first outer surface extending in the longitudinal direction and having the electrode pads disposed thereon, and the second outer surface extending in the longitudinal direction and intersecting the first outer surface, said chamfered portion including a rear end chamfered portion making a first chamfer angle with a rear end portion of the first outer surface and a leading end chamfered portion making a second chamfer angle with a leading end portion of the first outer surface, said first chamfer angle being larger than said second chamfer angle, and said second chamfer angle being greater than zero, and the electrode pads are arranged adjacent to the chamfered portions.

2. The gas sensor according to claim 1, wherein said second chamfer angle of the chamfered portion is 30° or more.

3. The gas sensor as claimed in claim 1, wherein the chamfered portion has an intermediate chamfered portion that is formed between the rear end chamfered portion and leading end chamfered portion, and the intermediate chamfered portion is chamfered at a third chamfer angle equal to or smaller than the first chamfer angle of the rear end chamfered portion and equal to or larger than the second chamfer angle of the leading end chamfered portion.

4. The gas sensor as claimed in claim 3, further comprising:

a separator, disposed so as to cover the rear end portion of the gas sensor element, and in which output terminals connected to the electrode pads are provided, wherein the intermediate chamfered portion is formed so as to be positioned closer to a rear end side in the longitudinal direction than a leading end position of the separator.

5. The gas sensor as claimed in claim 3, further comprising a heater element, disposed in the longitudinal direction of the gas sensor element and having at least a heating resistor disposed in a leading end portion thereof, stacked on the detecting element, wherein the intermediate chamfered portion is formed so as to be positioned closer to the rear end side in the longitudinal direction than a rear end position of the heating resistor.

6. The gas sensor as claimed in claim 3, wherein the intermediate chamfered portion is formed so that the third chamfer angle increases from a leading end side toward the rear end side in the longitudinal direction.

7. The gas sensor as claimed in claim 1, wherein the chamfer length of the leading end chamfered portion is 0.1 mm or more.

8. A gas sensor, comprising:

a gas sensor element including a plate-shaped detecting element extending in a longitudinal direction, a sensing portion disposed in a leading end portion in the longitudinal direction of the detecting element and detecting a specified gas in a gas to be measured, and a plurality of electrode pads disposed on an outer surface in a rear end portion in the longitudinal direction of the detecting element, at least one of the electrode pads outputting a detection signal from the sensing portion to an external circuit; and a housing that encloses the periphery of the gas sensor element, wherein the gas sensor element has at least one chamfered portion linking a first outer surface and a second outer surface of the detecting element, the first outer surface extending in the longitudinal direction and having the electrode pads disposed thereon, and the second outer surface extending in the longitudinal direction and intersecting the first outer surface, the chamfered portion has an intermediate chamfered portion that is formed between the rear end chamfered portion and leading end chamfered portion, and the intermediate chamfered portion is chamfered in a chamfer amount equal to or larger than the chamfer amount of the leading end chamfered portion, a chamfer length of the chamfered portion in a direction parallel to the first outer surface is formed so that a chamfer length of a rear end chamfered portion provided in the rear end portion is shorter than a chamfer length of a leading end chamfered portion provided in the leading end portion, said rear end chamfered portion is chamfered in a constant chamfer amount and the leading end chamfered portion is chamfered in a constant chamfer amount, and the chamfer amount of the leading end chamfered portion is greater than the chamfer amount of the rear end chamfered portion, and the electrode pads are arranged adjacent to the chamfered portions.

9. The gas sensor as claimed in claim 8, wherein the chamfer length of the leading end chamfered portion is 0.1 mm or more.

10. The gas sensor as claimed in claim 8, wherein the chamfer angle of the chamfered portion is 30° or more.

\* \* \* \* \*